(12) United States Patent
Kim et al.

(10) Patent No.: US 12,125,980 B2
(45) Date of Patent: Oct. 22, 2024

(54) ELECTROLYTE FOR LITHIUM SECONDARY BATTERY AND LITHIUM SECONDARY BATTERY INCLUDING THE SAME

(71) Applicant: LG Energy Solution, Ltd., Seoul (KR)

(72) Inventors: Gwang Yeon Kim, Daejeon (KR); Jeong Woo Oh, Daejeon (KR); Chul Haeng Lee, Daejeon (KR); Hyung Tae Kim, Daejeon (KR)

(73) Assignee: LG Energy Solution, Ltd., Seoul (KR)

( * ) Notice: Subject to any disclaimer, the term of this patent is extended or adjusted under 35 U.S.C. 154(b) by 710 days.

(21) Appl. No.: 17/311,831

(22) PCT Filed: Dec. 12, 2019

(86) PCT No.: PCT/KR2019/017622
§ 371 (c)(1),
(2) Date: Jun. 8, 2021

(87) PCT Pub. No.: WO2020/122650
PCT Pub. Date: Jun. 18, 2020

(65) Prior Publication Data
US 2022/0021030 A1    Jan. 20, 2022

(30) Foreign Application Priority Data

Dec. 13, 2018  (KR) .......................... 10-2018-0160981
Dec. 11, 2019  (KR) .......................... 10-2019-0164881

(51) Int. Cl.
| | | |
|---|---|---|
| H01M 10/0567 | (2010.01) | |
| C07C 271/24 | (2006.01) | |
| H01M 10/0525 | (2010.01) | |
| H01M 10/0568 | (2010.01) | |
| H01M 10/0569 | (2010.01) | |

(52) U.S. Cl.
CPC ....... H01M 10/0567 (2013.01); C07C 271/24 (2013.01); H01M 10/0525 (2013.01); H01M 10/0568 (2013.01); H01M 10/0569 (2013.01); H01M 2300/0025 (2013.01)

(58) Field of Classification Search
CPC ......... H01M 10/0567; H01M 10/0525; H01M 10/0568; H01M 10/0569; H01M 2300/0025; H01M 10/052; H01M 10/4235; C07C 271/24; Y02E 60/10
See application file for complete search history.

(56) References Cited

U.S. PATENT DOCUMENTS

| | | |
|---|---|---|
| 6,927,001 B1 | 8/2005 | Hamamoto et al. |
| 2006/0177742 A1* | 8/2006 | Abe ................. H01M 10/0568 429/330 |
| 2009/0053598 A1 | 2/2009 | Abe et al. |
| 2010/0239919 A1 | 9/2010 | Abe et al. |
| 2012/0183864 A1 | 7/2012 | Abe et al. |
| 2013/0052541 A1 | 2/2013 | Abe et al. |
| 2017/0229735 A1* | 8/2017 | Ahn .................. H01M 10/0567 |
| 2017/0346127 A1 | 11/2017 | Zhang et al. |
| 2018/0090748 A1 | 3/2018 | Mochizuki et al. |
| 2018/0301758 A1 | 10/2018 | Abe et al. |
| 2018/0342767 A1* | 11/2018 | Ahn ..................... H01M 4/525 |
| 2019/0058216 A1 | 2/2019 | Oh et al. |
| 2019/0198925 A1 | 6/2019 | Lee et al. |

FOREIGN PATENT DOCUMENTS

| | | |
|---|---|---|
| CN | 101107745 A | 1/2008 |
| CN | 107658498 A | 2/2018 |
| CN | 107735887 A | 2/2018 |
| CN | 108140889 A | 6/2018 |
| CN | 108352569 A | 7/2018 |
| EP | 1650826 A1 | 4/2006 |
| EP | 3361546 A1 | 8/2018 |
| EP | 3699997 A1 | 8/2020 |
| JP | 3951486 B2 | 8/2007 |
| JP | 2014235986 A | 12/2014 |
| JP | 2015195135 A | 11/2015 |
| KR | 20060035767 A | 4/2006 |
| KR | 101201272 B1 | 11/2012 |
| KR | 20160040127 A | 4/2016 |
| KR | 20180026358 A | 3/2018 |
| KR | 20180065958 A | 6/2018 |
| KR | 20180083272 A | 7/2018 |
| WO | 2013002322 A1 | 1/2013 |
| WO | 2016063964 A1 | 4/2016 |

OTHER PUBLICATIONS

Search report from International Application No. PCT/KR2019/017622, mailed Mar. 20, 2020.
Wong, D. H. C., et al., "Nonflammable perfluoropolyether-based electrolytes for lithium batteries." Proceedings of the National Acadamy of Sciences of the United States of America, vol. 111, No. 9, Mar. 4, 2014, pp. 3327-3331.
Extended European Search Report for Application No. 19895475.2 dated Nov. 30, 2021, pp. 1-5.

* cited by examiner

*Primary Examiner* — Daniel S Gatewood
(74) *Attorney, Agent, or Firm* — Lerner David LLP

(57) ABSTRACT

An electrolyte for a lithium secondary battery, and a lithium secondary battery including the same are disclosed herein. In some embodiments, an electrolyte for a lithium secondary battery includes a lithium salt having a molar concentration of 1.5 M to 2.0 M, an oligomer containing a unit represented by Formula 1 and having an acrylate group at an end thereof, a first additive represented by Formula 2, and an organic solvent.

11 Claims, No Drawings

ELECTROLYTE FOR LITHIUM SECONDARY BATTERY AND LITHIUM SECONDARY BATTERY INCLUDING THE SAME

CROSS-REFERENCE TO RELATED APPLICATIONS

The present application is a national phase entry under 35 U.S.C. § 371 of International Application No. PCT/KR2019/017622, filed on Dec. 12, 2019, which claims priority from Korean Patent Application Nos. 10-2018-0160981, filed on Dec. 13, 2018, and 10-2019-0164881, filed on Dec. 11, 2019, the disclosures of which are incorporated by reference herein.

TECHNICAL FIELD

The present invention relates to an electrolyte for a lithium secondary battery and a lithium secondary battery including the same, and more particularly, to an electrolyte for a lithium secondary battery, in which high-temperature performance and rapid charging performance are improved, and a lithium secondary battery including the same.

BACKGROUND ART

Applications of lithium secondary batteries have been rapidly expanded from power sources of portable devices, such as mobile phones, notebook computers, digital cameras, and camcorders, to power sources of medium and large sized devices s power tools, electric bicycles, hybrid electric vehicles (HEVs), and plug-in hybrid electric vehicles (plug-in HEVs, PHEVs). Appearance and size of the batteries have also changed in various ways as these application areas expand and demand increases. In order to meet these needs, battery components must be able to achieve stable battery performance under high current conditions.

A lithium secondary battery is prepared by using materials capable of intercalating and deintercalating lithium ions as a negative electrode and a positive electrode, optionally including a separator between the two electrodes, and disposing an electrolyte between both electrodes, wherein electricity is generated or consumed by oxidation and reduction reactions caused by the intercalation and deintercalation of the lithium ions into and from the positive electrode and the negative electrode.

With the recent expansion of the application areas, utilization and importance of the lithium secondary batteries have been gradually increased, and, particularly, there is a need for research and development on rapid charging of the lithium secondary battery while having excellent high-temperature performance of the lithium secondary battery. However, in a case in which charging time of a currently commercially available lithium secondary battery is shortened, since capacity and life characteristics of the battery are reduced, commercialization is difficult. With respect to a conventional fast charging method, since total energy density of the battery is low, there are limitations in industrial application.

Thus, it is time to study an electrolyte for a lithium secondary battery having improved fast charging performance in order to shorten the charging time while maintaining high-temperature capacity performance and output performance of the conventional lithium secondary battery.

PRIOR ART DOCUMENT

Korean Patent Application Laid-open Publication No. 10-2016-0040127

DISCLOSURE OF THE INVENTION

Technical Problem

An aspect of the present invention provides an electrolyte for a lithium secondary battery, in which rapid charging performance is improved while high-temperature performance of the lithium secondary battery is excellent, and a lithium secondary battery including the same.

Technical Solution

According to an aspect of the present invention, there is provided an electrolyte for a lithium secondary battery which includes: a lithium salt having a molar concentration of 1.5 M to 2.0 M; an oligomer containing a unit represented by Formula 1 and having an acrylate group at an end thereof; a first additive represented by Formula 2; and an organic solvent.

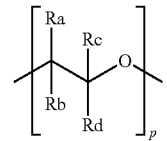

[Formula 1]

In Formula 1, $R_a$, $R_b$, $R_c$, and $R_d$ are each independently a fluorine element or an alkyl group having 1 to 3 carbon atoms which is unsubstituted or substituted with a fluorine element, and p is an integer of 1 to 50.

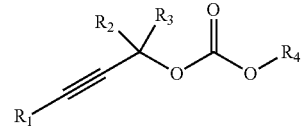

[Formula 2]

In Formula 2, $R_1$ to $R_4$ are each independently selected from the group consisting of hydrogen and a substituted or unsubstituted alkyl group having 1 to 5 carbon atoms.

According to another aspect of the present invention, there is provided a lithium secondary battery including the electrolyte for a lithium secondary battery of the present invention.

Advantageous Effects

Since an electrolyte for a lithium secondary battery according to the present invention includes specific oligomer and additive while having excellent high-temperature performance, it may also improve rapid charging performance of the battery.

MODE FOR CARRYING OUT THE INVENTION

Hereinafter, the present invention will be described in more detail.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

The terminology used herein is for the purpose of describing particular example embodiments only and is not intended to be limiting of the present invention. In the specification, the terms of a singular form may comprise plural forms unless referred to the contrary.

It will be further understood that the terms "include," "comprise," or "have" when used in this specification, specify the presence of stated features, numbers, steps, elements, or combinations thereof, but do not preclude the presence or addition of one or more other features, numbers, steps, elements, or combinations thereof.

In the present specification, the expression "weight-average molecular weight" may denote a standard polystyrene-equivalent value measured by gel permeation chromatography (GPC), and, unless otherwise specified, a molecular weight may denote the weight-average molecular weight. For example, in the present invention, the GPC conditions are as follows: the weight-average molecular weight is measured by using 1200 series by Agilent Technologies, a PL mixed B column by Agilent Technologies may be used in this case, and tetrahydrofuran (THE) may be used as a solvent.

Electrolyte for Lithium Secondary Battery

The present invention provides an electrolyte for a lithium secondary battery which includes: a lithium salt having a molar concentration of 1.5 M to 2.0 M; an oligomer containing a unit represented by Formula 1 and having an acrylate group at an end thereof; a first additive represented by Formula 2; and an organic solvent.

In a case in which the lithium salt is included within the above molar concentration range, since lithium ions are sufficiently supplied, output characteristics of the battery may be improved by improving a lithium ion yield (Lit transference number) and a degree of dissociation of the lithium ions.

Any compound capable of providing lithium ions and used in a lithium secondary battery may be used as the lithium salt without particular limitation, and, specifically, the lithium salt may include $Li^+$ as a cation, and one selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $AsF_6^-$, $BF_2C_2O_4^-$, $BC_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $CF_3(CF_2)_7SO_3^-$, $CF_3CO_2^-$, $CH_3CO_2^-$, $SCN^-$, and $(CF_3CF_2SO_2)_2N^-$ or, if necessary, a mixture of two or more thereof may be used as an anion.

Specifically, the lithium salt may include $LiPF_6$ and a lithium imide salt.

In this case, the lithium imide salt may include at least one selected from the group consisting of $Li(CF_3SO_2)_2N$, $Li(FSO_2)_2N$, and $Li(CF_3CF_2SO_2)_2N$.

In a case in which the lithium salt includes the $LiPF_6$ and the lithium imide salt, the $LiPF_6$ and the lithium imide salt may be mixed in a molar ratio of 1:1 to 1:5, preferably 1:1 to 1:4, and more preferably 1:1 to 1:3. In a case in which the two types of salts are mixed in the above molar ratio and used, the output characteristics of the battery may be improved while minimizing a corrosion phenomenon in the battery due to the electrolyte.

(2) Oligomer

The electrolyte for a lithium secondary battery of the present invention includes an oligomer containing a unit represented by Formula 1 and having an acrylate group at an end thereof.

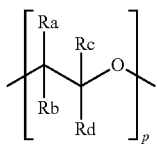

[Formula 1]

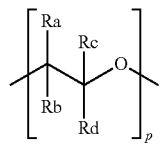

[Formula 1]

In Formula 1, $R_a$, $R_b$, $R_c$, and $R_d$ are each independently a fluorine element or an alkyl group having 1 to 3 carbon atoms which is unsubstituted or substituted with a fluorine element, and p is an integer of 1 to 50.

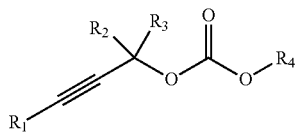

[Formula 2]

In Formula 2, $R_1$ to $R_4$ are each independently selected from the group consisting of hydrogen and a substituted or unsubstituted alkyl group having 1 to 5 carbon atoms.

(1) Lithium Salt

The lithium salt may be included in a molar concentration of 1.5 M to 2.0 M, preferably 1.5 M to 1.9 M, and more preferably 1.5 M to 1.8 M in the electrolyte for a lithium secondary battery.

In Formula 1, $R_a$, $R_b$, $R_c$, and $R_d$ are each independently a fluorine element or an alkyl group having 1 to 3 carbon atoms which is unsubstituted or substituted with a fluorine element, and p is an integer of 1 to 50.

Since the oligomer containing a unit represented by Formula 1 and having an acrylate group at an end thereof includes an ethylene group substituted with a fluorine element having low reactivity with lithium ions, a side reaction of the lithium ions and a decomposition reaction of the lithium salt may be controlled, and thus, a side reaction, which occurs when the high-concentration lithium salt is used, may be suppressed. Also, since the oligomer contains a fluorine element with excellent flame retardancy, heat generation and ignition phenomenon of the lithium secondary battery are suppressed when the electrolyte including the oligomer is used, and thus, high-temperature safety may be improved.

Since the oligomer contains the hydrophilic acrylate group at the end as well as the unit containing the hydrophobic fluorine element, the oligomer may act as a surfactant to reduce surface resistance with an electrode interface and improve wetting in the lithium secondary battery.

Specifically, oligomer may be an oligomer represented by Formula 1A below.

[Formula 1A]

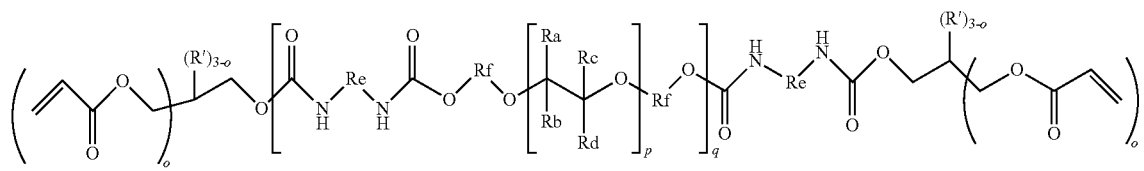

In Formula 1A, $R_a$, $R_b$, $R_c$, and $R_d$ are each independently a fluorine element or an alkyl group having 1 to 3 carbon atoms which is unsubstituted or substituted with a fluorine element, $R_e$ is an aliphatic hydrocarbon group or an aromatic hydrocarbon group, $R_f$ is an alkylene group having 1 to 5 carbon atoms which is unsubstituted or substituted with a fluorine element, R' is hydrogen or an alkyl group having 1 to 3 carbon atoms, o is an integer of 1 to 3, p is an integer of 1 to 50, and q is an integer of 1 to 15. In this case, p may preferably be an integer of 1 to 45, and may more preferably be an integer of 1 to 40.

In the oligomer represented by Formula 1A, the aliphatic hydrocarbon group includes an alicyclic hydrocarbon group or a linear hydrocarbon group.

The alicyclic hydrocarbon group may include at least one selected from the group consisting of a substituted or unsubstituted cycloalkylene group having 4 to 20 carbon atoms; a substituted or unsubstituted cycloalkylene group having 4 to 20 carbon atoms which contains an isocyanate group (NCO); a substituted or unsubstituted cycloalkenylene group having 4 to 20 carbon atoms; and a substituted or unsubstituted heterocycloalkylene group having 2 to 20 carbon atoms.

The linear hydrocarbon group may include at least one selected from the group consisting of a substituted or unsubstituted alkylene group having 1 to 20 carbon atoms; a substituted or unsubstituted alkylene group having 1 to 20 carbon atoms which contains an isocyanate group (NCO); a substituted or unsubstituted alkoxylene group having 1 to 20 carbon atoms; a substituted or unsubstituted alkenylene group having 2 to 20 atoms; and carbon a substituted or unsubstituted alkynylene group having 2 to 20 carbon atoms.

Furthermore, in the oligomer represented by Formula 1A, the aromatic hydrocarbon group may include a substituted or unsubstituted arylene group having 6 to 20 carbon atoms; or a substituted or unsubstituted heteroarylene group having 2 to 20 carbon atoms.

As a specific example, the oligomer represented by Formula 1A may be an oligomer represented by Formula 1A-1 below.

[Formula 1A-1]

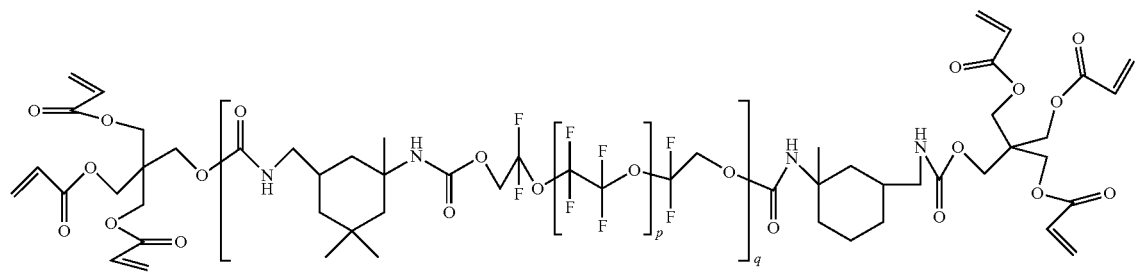

In Formula 1A-1, p is an integer of 1 to 50, and q is an integer of 1 to 15. p may preferably be an integer of 1 to 45, and may more preferably be an integer of 1 to 40.

Also, the oligomer may be an oligomer represented by Formula 1B below.

[Formula 1B]

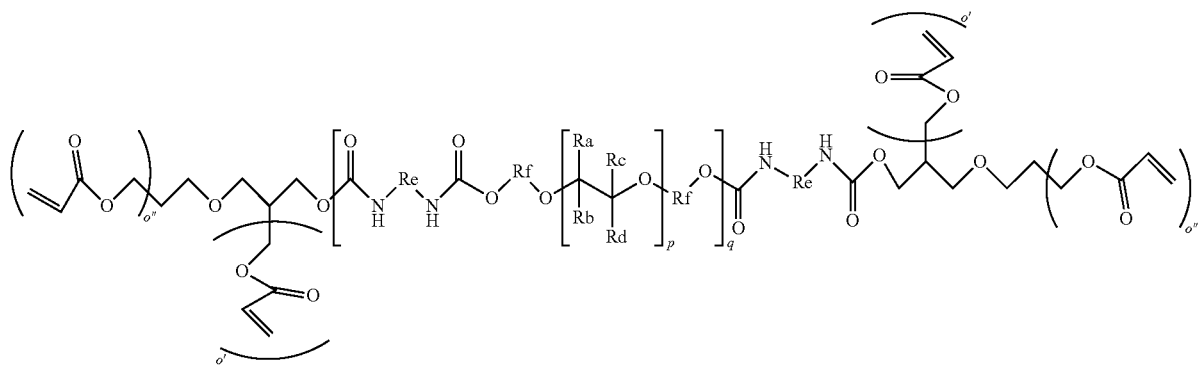

In Formula 1B, $R_a$, $R_b$, $R_c$, and $R_d$ are each independently a fluorine element or an alkyl group having 1 to 3 carbon atoms which is substituted or unsubstituted with a fluorine element, $R_e$ is an aliphatic hydrocarbon group or an aromatic hydrocarbon group, $R_f$ is an alkylene group having 1 to 5 carbon atoms which is substituted or unsubstituted with a fluorine element, o' is an integer of 1 to 2, o" is an integer of 1 to 3, p is an integer of 1 to 50, and q is an integer of 1 to 15. p may preferably be an integer of 1 to 45, and may more preferably be an integer of 1 to 40.

As a specific example, the oligomer represented by Formula 1B may be an oligomer represented by Formula 1B-1 below.

In this case, the oligomer may be included in an amount of 0.1 part by weight to 1 part by weight, preferably 0.1 part by weight to 0.9 part by weight, and more preferably 0.1 part by weight to 0.8 part by weight based on 100 parts by weight of the electrolyte for a lithium secondary battery. In a case in which the oligomer is included in an amount within the above range, since mobility and ionic conductivity of lithium ions are maintained above a predetermined level, the oligomer may act as a surfactant while a side reaction is suppressed, and thus, interfacial resistance in the battery may be minimized.

(3) First Additive

Next, a first additive represented by the following Formula 2 will be described.

[Formula 1B-1]

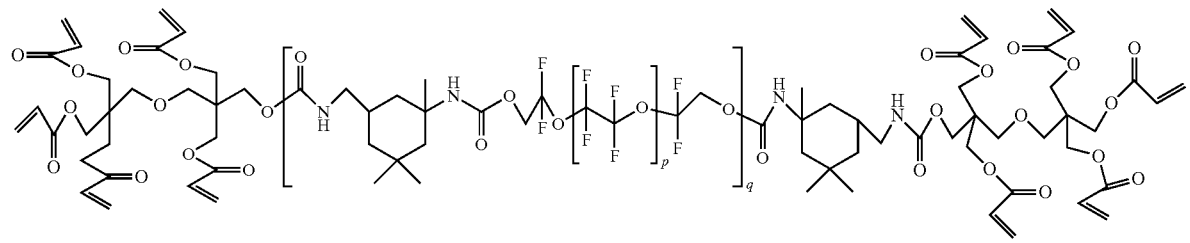

In Formula 1B-1, p is an integer of 1 to 50, and q is an integer of 1 to 15. In this case, p may preferably be an integer of 1 to 45, and may more preferably be an integer of 1 to 40.

A weight-average molecular weight (Mw) of the oligomer may be controlled by the number of repeating units, and may be in a range of about 500 g/mol to about 200,000 g/mol, particularly 1,000 g/mol to 150,000 g/mol, and more particularly 2,000 g/mol to 100,000 g/mol. In a case in which the weight-average molecular weight of the oligomer is within the above range, the oligomer may be well dispersed due to high affinity with the organic solvent, wetting of the electrolyte may be improved by reducing the surface tension below a predetermined level, the decomposition reaction of the lithium salt may be suppressed, and a side reaction caused by lithium ions may be prevented.

[Formula 2]

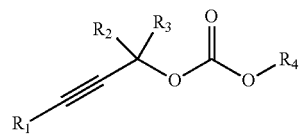

In Formula 2, $R_1$ to $R_4$ are each independently selected from the group consisting of hydrogen and a substituted or unsubstituted alkyl group having 1 to 5 carbon atoms.

With respect to the first additive represented by Formula 2, since LUMO (Lowest Unoccupied Molecular Orbital), the lowest energy orbital among molecular orbitals without electrons, is low, reduction decomposition at a negative electrode is rapid and a propargyl group containing carbon-carbon triple bonds forms an SEI (Solid Electrolyte Interphase) on a surface of the negative electrode to prevent adhesion of metal ions dissolved from a positive electrode active material to the negative electrode, and thus, the first additive may improve performance degradation of the battery.

As a specific example, the first additive may be one represented by Formula 2A below.

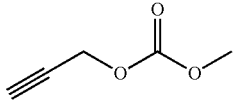

[Formula 2A]

The first additive may be included in an amount of 0.1 part by weight to 1 part by weight, preferably 0.1 part by weight to 0.8 part by weight, and more preferably 0.1 part by weight to 0.6 part by weight based on 100 parts by weight of the electrolyte for a lithium secondary battery. In a case in which the first additive is included in an amount within the above range, an SEI may be stably formed on the surface of the negative electrode while an increase in resistance is minimized, and the adhesion of the metal ions dissolved from the positive electrode active material to the negative electrode may be prevented.

(4) Organic Solvent

Next, the organic solvent will be described.

Any organic solvent typically used in an electrolyte for a lithium secondary battery may be used as the organic solvent without limitation. For example, a cyclic carbonate compound, a linear carbonate compound, an ether compound, an ester compound, or an amide compound may be used alone or as a mixture of two or more thereof.

Specific examples of the cyclic carbonate compound may be any one selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and fluoroethylene carbonate (FEC), or a mixture of two or more thereof.

Also, as a specific example of the linear carbonate compound, dimethyl carbonate (DMC) may be used. In addition to the dimethyl carbonate, ethyl methyl carbonate (EMC), methyl propyl carbonate, or ethyl propyl carbonate are present as the linear carbonate compound, but, since the dimethyl carbonate has a smaller molecular size than other linear carbonate compounds and has low viscosity characteristics, the dimethyl carbonate may further improve ionic conductivity of the electrolyte in comparison to a case where other linear carbonate compounds are used.

In particular, cyclic carbonates, such as ethylene carbonate, which are known to well dissociate the lithium salt in the electrolyte due to high permittivity as highly viscous organic solvents, among the carbonate-based organic solvents may be used, and an electrolyte having high electrical conductivity may be prepared when the cyclic carbonate is mixed with low viscosity, low permittivity linear carbonate, such as dimethyl carbonate, in an appropriate ratio and used.

Furthermore, as the ether compound, any one selected from the group consisting of dimethyl ether, diethyl ether, dipropyl ether, methylethyl ether, methylpropyl ether, and ethylpropyl ether, or a mixture of two or more thereof may be used, but the present invention is not limited thereto.

As the ester compound, any one selected from the group consisting of linear esters, such as methyl acetate, ethyl acetate, propyl acetate, methyl propionate, ethyl propionate, propyl propionate, and butyl propionate; and cyclic esters, such as γ-butyrolactone, γ-valerolactone, γ-caprolactone, σ-valerolactone, and ε-caprolactone, or mixture of two or more thereof may be used, but the present invention is not limited thereto.

(5) Second Additive

The electrolyte for a lithium secondary battery according to the present invention may further include a second additive. As a specific example of the second additive, at least one compound selected from the group consisting of vinylene carbonate (VC), 1,3-propane sultone (PS), ethylene sulfate (ESa), fluorinated benzene (FB), and $LiBF_4$ may be used as the additive. Particularly, in a case in which the above-listed compounds are used together as the second additive, a stable film may be formed on both positive electrode and negative electrode at the same time. In this case, since the decomposition of the electrolyte may not only be suppressed even under high-temperature and high-pressure conditions by the film formed on the negative electrode, but dissolution of transition metal included in the positive electrode may also be suppressed by the film formed on the positive electrode, high-temperature and high-pressure characteristics and stability of the battery may be improved.

In this case, the second additive may be included in an amount of 1 part by weight to 15 parts by weight, preferably 1 part by weight to 12 parts by weight, and more preferably 1 part by weight to 11 parts by weight based on 100 parts by weight of the electrolyte for a lithium secondary battery. In a case in which the second additive is included in an amount within the above range, the occurrence of a side reaction during an initial activation process of the secondary battery or the remaining or precipitation of the additive may be prevented while a film may be stably formed on the electrode and an ignition phenomenon may be suppressed during overcharge.

Lithium Secondary Battery

Next, a lithium secondary battery according to the present invention will be described.

The lithium secondary battery according to an embodiment of the present invention includes at least one positive electrode, at least one negative electrode, a separator which may be optionally disposed between the positive electrode and the negative electrode, and the electrolyte for a lithium secondary battery. In this case, since the electrolyte for a lithium secondary battery is the same as described above, a detailed description thereof will be omitted.

(1) Positive Electrode

The positive electrode may be prepared by coating a positive electrode collector with a positive electrode active material slurry including a positive electrode active material, a binder for an electrode, an electrode conductive agent, and a solvent.

The positive electrode collector is not particularly limited so long as it has conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used. In this case, the positive electrode collector may have fine surface roughness to improve bonding strength with the positive electrode active material, and the positive electrode collector may be used in various shapes such as a film, a sheet, a foil, a net, a porous body, a foam body, a non-woven fabric body, and the like.

The positive electrode active material is a compound capable of reversibly intercalating and deintercalating lithium, wherein the positive electrode active material may specifically include a lithium composite metal oxide including lithium and at least one metal such as cobalt, manganese, nickel, or aluminum. Specifically, the lithium composite metal oxide may include lithium-manganese-based oxide (e.g., $LiMnO_2$, $LiMn_2O_4$, etc.), lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-Y1}Mn_{Y1}O_2$ (where $0<Y1<1$), $LiMn_{2-Z1}Ni_{Z1}O_4$ (where $0<Z1<2$), etc.), lithium-nickel-cobalt-based oxide (e.g., $LiNi_{1-Y2}CO_{Y2}O_2$ (where $0<Y2<1$), lithium-manganese-cobalt-based oxide (e.g., $LiCo_{1-Y3}Mn_{Y3}O_2$ (where $0<Y3<1$), $LiMn_{2-Z2}CO_{Z2}O_4$ (where $0<Z2<2$), etc.), lithium-nickel-manganese-cobalt-based oxide (e.g., $Li(Ni_{p1}Co_{q1}Mn_{r1})O_2$ (where $0<p1<1$, $0<q1<1$, $0<r1<1$, and $p1+q1+r1=1$) or $Li(Ni_{p2}CO_{q2}Mn_{r2})O_4$ (where $0<p2<2$, $0<q2<2$, $0<r2<2$, and $p2+q2+r2-2$), etc.), or lithium-nickel-cobalt-transition metal (M) oxide (e.g., $Li(Ni_{p3}CO_{q3}Mn_{r3}M_{S1})$ $O_2$ (where M is selected from the group consisting of aluminum (Al), iron (Fe), vanadium (V), chromium (Cr), titanium (Ti), tantalum (Ta), magnesium (Mg), and molybdenum (Mo), and p3, q3, r3, and s1 are atomic fractions of each independent elements, wherein $0<p3<1$, $0<q3<1$, $0<r3<1$, $0<S1<1$, and $p3+q3+r3+S1=1$), etc.), and any one thereof or a compound of two or more thereof may be included.

Among these materials, in terms of the improvement of capacity characteristics and stability of the battery, the composite metal oxide may include $LiCoO_2$, $LiMnO_2$, lithium $LiNiO_2$, lithium nickel manganese cobalt oxide (e.g., $Li(Ni_{0.6}Mn_{0.2}Co_{0.2})O_2$, $Li(Ni_{0.5}Mn_{0.3}Co_{0.2})O_2$, or $Li(Ni_{0.8}Mn_{0.1}Co_{0.1})$ $O_2$), or lithium nickel cobalt aluminum oxide (e.g., $LiNi_{0.8}Co_{0.15}Al_{0.05}O_2$, etc.), and, in consideration of a significant improvement due to the control of type and content ratio of elements constituting the lithium composite metal oxide, the lithium composite metal oxide may include $Li(Ni_{0.6}Mn_{0.2}Co_{0.2})O_2$, $Li(Ni_{0.5}Mn_{0.3}Co_{0.2})$ $O_2$, $Li(Ni_{0.7}Mn_{0.15}Co_{0.15})$ $O_2$, or $Li(Ni_{0.8}Mn_{0.1}Co_{0.1})O_2$, and any one thereof or a mixture of two or more thereof may be used.

The binder for an electrode is a component that assists in the binding between the positive electrode active material and the electrode conductive agent and in the binding with the current collector. Specifically, the binder may include polyvinylidene fluoride, polyvinyl alcohol, carboxymethylcellulose (CMC), starch, hydroxypropylcellulose, regenerated cellulose, polyvinylpyrrolidone, polytetrafluoroethylene, polyethylene (PE), polypropylene, an ethylene-propylene-diene terpolymer (EPDM), a sulfonated EPDM, a styrene-butadiene rubber, a fluoro rubber, various copolymers, and the like.

The electrode conductive agent is a component for further improving the conductivity of the positive electrode active material. Any electrode conductive agent may be used without particular limitation so long as it has conductivity without causing adverse chemical changes in the battery, and, for example, a conductive material, such as: graphite; a carbon-based material such as carbon black, acetylene black, Ketjen black, channel black, furnace black, lamp black, and thermal black; conductive fibers such as carbon fibers or metal fibers; powder such as fluorocarbon powder, aluminum powder, and nickel powder; conductive whiskers such as zinc oxide whiskers and potassium titanate whiskers; conductive metal such oxide titanium oxide; or as polyphenylene derivatives, may be used. Specific examples of a commercial conductive agent may include acetylene black-based products (Chevron Chemical Company, Denka black (Denka Singapore Private Limited), or Gulf Oil Company), Ketjen black, ethylene carbonate (EC)-based products (Armak Company), Vulcan XC-72 (Cabot Company), and Super P (Timcal Graphite & Carbon).

The solvent may include an organic solvent, such as N-methyl-2-pyrrolidone (NMP), and may be used in an amount such that desirable viscosity is obtained when the positive electrode active material as well as optionally the binder for a positive electrode and the positive electrode conductive agent is included.

(2) Negative Electrode

The negative electrode, for example, may be prepared by coating a negative electrode collector with a negative electrode active material slurry including a negative electrode active material, a binder for an electrode, an electrode conductive agent, and a solvent. A metal current collector itself may be used as the negative electrode.

The negative electrode collector is not particularly limited so long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, an aluminum-cadmium alloy, or the like may be used. Also, similar to the positive electrode collector, the negative electrode collector may have fine surface roughness to improve bonding strength with the negative electrode active material, and the negative electrode collector may be used in various shapes such as a film, a sheet, a foil, a net, a porous body, a foam body, a non-woven fabric body, and the like.

The negative electrode active material may include at least one negative electrode active material selected from the group consisting of natural graphite, artificial graphite, a carbonaceous material; lithium-containing titanium composite oxide (LTO); metals (Me) such as silicon (Si), tin (Sn), lithium (Li), zinc (Zn), Mg, cadmium (Cd), cerium (Ce), nickel (Ni), or Fe; alloys composed of the metals (Me); oxides (MeOx) of the metals (Me); and composites of the metals (Me) and carbon.

Since the binder for an electrode, the electrode conductive agent, and the solvent are the same as described above, detailed descriptions thereof will be omitted.

(3) Separator

A typical porous polymer film used as a typical separator, for example, a porous polymer film prepared from a polyolefin-based polymer, such as an ethylene homopolymer, a propylene homopolymer, an ethylene-butene copolymer, an ethylene-hexene copolymer, and an ethylene-methacrylate copolymer, may be used alone or in a lamination therewith as the separator. Also, a typical porous nonwoven fabric, for example, a nonwoven fabric formed of high melting point glass fibers or polyethylene terephthalate fibers may be used, but the present invention is not limited thereto.

Hereinafter, the present invention will be described in detail, according to specific examples. However, the following examples are merely presented to exemplify the present invention, and the scope of the present invention is not limited thereto. It will be apparent to those skilled in the art that various modifications and alterations are possible within the scope and technical spirit of the present invention. Such modifications and alterations fall within the scope of claims included herein.

EXAMPLES

Example 1

(1) Preparation of Electrolyte for Lithium Secondary Battery

A non-aqueous organic solvent was prepared by adding $LiPF_6$ to an organic solvent including ethylene carbonate (EC) and dimethyl carbonate (DMC) at a volume ratio of 1:9 such that a molar concentration of the $LiPF_6$ was 1.5 M. 0.5 g of the oligomer (weight-average molecular weight (Mw): 5000, p=5, and q=3) represented by Formula 1A-1 and 0.5 g of the first additive represented by Formula 2A were added to 99 g of the non-aqueous organic solvent to prepare a liquid electrolyte for a lithium secondary battery.

(2) Positive Electrode Preparation

A positive electrode active material ($Li(Ni_{0.8}Co_{0.1}Mn_{0.1})O_2$, NCM811), a conductive agent (bundle-type carbon nanotubes), and a binder (polyvinylidene fluoride (PVDF)) were mixed in N-methyl-2-pyrrolidone (NMP), as a solvent, in a weight ratio of 97.7:0.3:2 to prepare a positive electrode active material slurry. A 20 μm thick positive electrode collector (aluminum (Al) thin film) was coated with the positive electrode active material slurry, dried, and roll-pressed to prepare a positive electrode.

(3) Negative Electrode Preparation

A negative electrode active material (graphite (AGP8)) and SiO were mixed in distilled water, as a solvent, in a weight ratio of 95:5 to prepare a negative electrode active material slurry. A 10 μm thick negative electrode collector (copper (Cu) thin film) was coated with the negative electrode active material slurry, dried, and roll-pressed to prepare a negative electrode.

(4) Lithium Secondary Battery Preparation

After an electrode assembly was prepared by sequentially stacking the positive electrode and negative electrode prepared by the above-described methods with a porous polyethylene film, as a separator, in the order of the positive electrode/separator/negative electrode, the electrode assembly was accommodated in a pouch-type secondary battery case, and the electrolyte for a lithium secondary battery was injected into the pouch-type secondary battery case to prepare a lithium secondary battery.

Example 2

A non-aqueous organic solvent was prepared by adding $LiPF_6$ and $Li(FSO_2)_2N$ (LiFSI) to an organic solvent including ethylene carbonate (EC) and dimethyl carbonate (DMC) at a volume ratio of 1:9 such that molar concentrations of the $LiPF_6$ and the $Li(FSO_2)_2N$ were 0.5 M and 1.0 M, respectively. 0.5 g of the oligomer (weight-average molecular weight (Mw): 5000, p=5, and q=3) represented by Formula 1A-1 and 0.5 g of the first additive represented by Formula 2A were added to 99 g of the non-aqueous organic solvent to prepare a liquid electrolyte for a lithium secondary battery.

A lithium secondary battery was prepared in the same manner as in Example 1 except that the liquid electrolyte for a lithium secondary battery was injected.

Example 3

A liquid electrolyte for a lithium secondary battery and a lithium secondary battery were prepared in the same manner as in Example 1 except that an organic solvent including ethylene carbonate (EC) and ethyl methyl carbonate (EMC) at a volume ratio of 1:9 was used when the electrolyte for a lithium secondary battery was prepared.

Example 4

A non-aqueous organic solvent was prepared by adding $LiPF_6$ to an organic solvent including ethylene carbonate (EC) and dimethyl carbonate (DMC) at a volume ratio of 1:9 such that a molar concentration of the $LiPF_6$ was 1.5 M. 0.5 g of the oligomer (weight-average molecular weight (Mw): 5000, p=5, and q=3) represented by Formula 1A-1, 0.5 g of the first additive represented by Formula 2A, and 3 g of vinylene carbonate (VC), as a second additive, were added to 96 g of the non-aqueous organic solvent to prepare a liquid electrolyte for a lithium secondary battery.

A lithium secondary battery was prepared in the same manner as in Example 1 except that the liquid electrolyte for a lithium secondary battery was injected.

Example 5

A liquid electrolyte for a lithium secondary battery and a lithium secondary battery were prepared in the same manner as in Example 1 except that 0.5 g of the oligomer (weight-average molecular weight (Mw): 5000, p=5, and q=3) represented by Formula 1A-1, 0.5 g of the first additive represented by Formula 2A, and 1 wt % of ethylene sulfate (ESa), 0.2 wt % of $LiBF_4$, and 6 wt % of fluorinated benzene (FB), as a second additive, were further added to 91.8 g of the non-aqueous organic solvent when the electrolyte for a lithium secondary battery was prepared.

COMPARATIVE EXAMPLES

Comparative Example 1

An electrolyte for a lithium secondary battery and a lithium secondary battery were prepared in the same manner as in Example 1 except that the oligomer was not added when the electrolyte for a lithium secondary battery was prepared.

Comparative Example 2

An electrolyte for a lithium secondary battery and a lithium secondary battery were prepared in the same manner as in Example 1 except that the first additive was not added when the electrolyte for a lithium secondary battery was prepared.

Comparative Example 3

An electrolyte for a lithium secondary battery and a lithium secondary battery were prepared in the same manner as in Example 1 except that $LiPF_6$ was added to have a molar concentration of 1.0 M when the electrolyte for a lithium secondary battery was prepared.

Comparative Example 4

An electrolyte for a lithium secondary battery and a lithium secondary battery were prepared in the same manner as in Example 1 except that $LiPF_6$ was added to have a molar concentration of 3.0 M when the electrolyte for a lithium secondary battery was prepared.

Comparative Example 5

An electrolyte for a lithium secondary battery and a lithium secondary battery were prepared in the same manner as in Example 1 except that both the oligomer and the first additive were not used when the electrolyte for a lithium secondary battery was prepared.

Experimental Examples

Experimental Example 1: Measurement of High-Temperature (45° C.) Capacity Retention After formation was performed on each of the lithium secondary batteries prepared in Examples 1 to 5 and Comparative Examples 1 to 5 at a current of 200 mA (0.1 C rate), discharge capacity in this case was set as initial capacity. Thereafter, constant current/constant voltage (CC/CV) charging at 660 mA (0.33 C, 0.05 C cut-off) to 4.2 V and CC discharging at 660 mA (0.33 C) to 2.5 V were performed 100 times at a high temperature (45° C.), respectively. Thereafter, 100th discharge capacity and the initial capacity were compared to calculate capacity retention, and the results thereof are presented in Table 1.

TABLE 1

|  | High-temperature (45° C.) capacity retention (%) |
| --- | --- |
| Example 1 | 89 |
| Example 2 | 90 |
| Example 3 | 85 |
| Example 4 | 92 |
| Example 5 | 93 |
| Comparative Example 1 | 80 |
| Comparative Example 2 | 82 |
| Comparative Example 3 | 79 |
| Comparative Example 4 | 70 |
| Comparative Example 5 | 76 |

Referring to Table 1, it may be confirmed that high-temperature capacity retentions of the lithium secondary batteries prepared according to the examples were higher than those of the lithium secondary batteries prepared according to the comparative examples.

Experimental Example 2: Measurement of High-Temperature (60° C.) Storage Characteristics Discharge capacity, after each of the lithium secondary batteries prepared in Examples 1 to 5 and Comparative Examples 1 to 5 was charged at 0.33 C rate under a constant current/constant voltage condition to 4.2 V, cut-off charged at 0.05 C, and discharged at 0.33 C to 2.5 V, was set as initial discharge capacity. Subsequently, each of the lithium secondary batteries was charged at 0.33 C rate under a constant current/constant voltage condition to 4.2 V and cut-off charged at 0.05 C, and remaining capacity over time was measured while being stored at 60° C. for 2 weeks. High-temperature capacity retentions (%) were calculated based on the initial discharge capacity (100%) and are presented in Table 2.

TABLE 2

|  | High-temperature (60° C.) capacity retention (%) |
| --- | --- |
| Example 1 | 90 |
| Example 2 | 91 |
| Example 3 | 92 |
| Example 4 | 87 |
| Example 5 | 92 |

TABLE 2-continued

|  | High-temperature (60° C.) capacity retention (%) |
| --- | --- |
| Comparative Example 1 | 82 |
| Comparative Example 2 | 81 |
| Comparative Example 3 | 78 |
| Comparative Example 4 | 75 |
| Comparative Example 5 | 81 |

Referring to Table 2, it may be confirmed that, even under a high-temperature condition, capacity retentions of the lithium secondary batteries prepared according to the examples were higher than those of the lithium secondary batteries prepared according to the comparative examples.

Experimental Example 3: Ionic Conductivity Measurement

Ionic conductivities of the electrolytes for a lithium secondary battery, which were prepared in Examples 1 and 3, were measured at −10° C., 0° C., and 25° C. using a probe-type ionic conductivity meter (probe: InLab 731, model: S470, manufacturer: Mettler Toledo). The measured ionic conductivities are presented in Table 3 below.

TABLE 3

|  | Ionic conductivity (−10° C., mS/cm) | Ionic conductivity (0° C., mS/cm) | Ionic conductivity (25° C., mS/cm) |
| --- | --- | --- | --- |
| Example 1 | 4.71 | 6.26 | 11.12 |
| Example 3 | 3.25 | 4.15 | 8.2 |

Referring to Table 3, it may be confirmed that ionic conductivity of Example 1, in which dimethyl carbonate, as linear carbonate having low viscosity and low permittivity, was used, among the examples was higher than that of Example 3 in which ethyl methyl carbonate, instead of the dimethyl carbonate, was used as linear carbonate.

Experimental Example 4: Rapid Charging Performance

After formation was performed on each of the lithium secondary batteries prepared in Examples 1 and 3 at a current of 200 mA (0.1 C rate), CC/CV charging at 660 mA (0.33 C, 0.05 C cut-off) to 4.2 V and CC discharging at 660 mA (0.33 C) to 2.5 V were repeated 3 times. In this case, $3^{rd}$ discharge capacity was defined as initial capacity.

After the measurement of the initial capacity, the lithium secondary batteries at a state of charge (SOC) of 8% were respectively charged at a low temperature (10° C.) in a CC mode under conditions of 1 C (SOC 8%→SOC 22%, 505s), 0.9 C (SOC 22%→SOC 28%, 226s), 0.8 C (SOC 28%→SOC 35%, 340s), 0.7 C (SOC 35%→SOC 45%, 501s), 0.6 C (SOC 45%→SOC 57%, 737s), 0.5 C. (SOC 57%→SOC 71%, 990s), and 0.4 C (SOC 71%→SOC 80%, 810s), and a voltage value was checked at 1 second intervals for each charging range.

Thereafter, charge was recorded when charged in a CC/CV mode by setting a termination condition with the voltage value for each range obtained in the CC mode and end time set in each range at a C-rate which was set for each SOC range from a SOC of 8% to 80% at a low temperature (10° C.). Each lithium secondary battery was again discharged to a SOC of 8% at 0.1 C in a CC mode. Thereafter, one charging/discharging process was defined as one cycle. Thereafter, charge capacity (%) after 50 cycles based on the initial charge capacity (100%) was defined as rapid charging capacity retention (%) and presented in Table 4.

TABLE 4

|  | Low-temperature (10° C.) rapid charging capacity retention (%) |
| --- | --- |
| Example 1 | 96 |
| Example 3 | 91 |

Referring to Table 4, it may be confirmed that rapid charging capacity retention of Example 1, in which dimethyl carbonate, as linear carbonate having low viscosity and low permittivity, was used, among the examples was higher than that of Example 3 in which ethyl methyl carbonate, instead of the dimethyl carbonate, was used as linear carbonate.

The invention claimed is:

1. An electrolyte for a lithium secondary battery, the electrolyte comprising:
   a lithium salt having a molar concentration of 1.5 M to 2.0 M;
   an oligomer containing a unit represented by Formula 1A or 1B;
   a first additive represented by Formula 2; and
   an organic solvent:

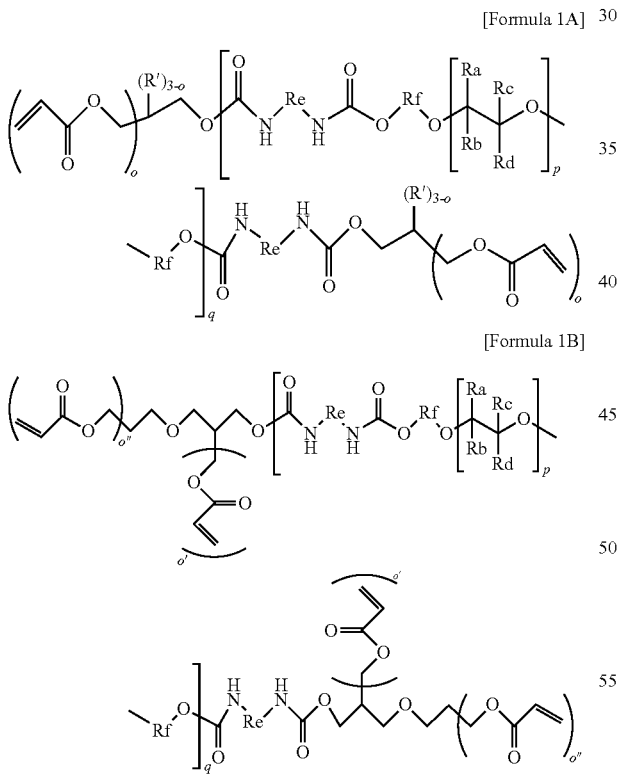

[Formula 1A]

[Formula 1B]

wherein, in Formulae 1A and 1B, $R_a$, $R_b$, $R_c$, and $R_d$ are each independently a fluorine element or an alkyl group having 1 to 3 carbon atoms which is unsubstituted or substituted with a fluorine element, $R_e$ is an aliphatic hydrocarbon group or an aromatic hydrocarbon group, $R_f$ is an alkylene group having 1 to 5 carbon atoms which is unsubstituted or substituted with a fluorine element, R' is hydrogen or an alkyl group having 1 to 3 carbon atoms, o is an integer of 1 to 3, o' is an integer of 1 to 2, o" is an integer of 1 to 3, p is an integer of 1 to 50, and q is an integer of 2 to 15,

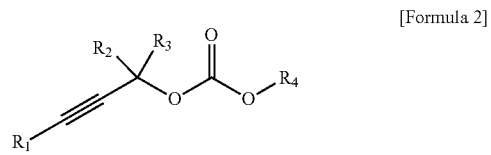

[Formula 2]

wherein, in Formula 2, $R_1$ to $R_4$ are each independently hydrogen or a substituted or unsubstituted alkyl group having 1 to 5 carbon atoms.

2. The electrolyte for a lithium secondary battery of claim 1, wherein the lithium salt comprises $LiPF_6$ and a lithium imide salt.

3. The electrolyte for a lithium secondary battery of claim 2, wherein a molar ratio of the $LiPF_6$ and the lithium imide salt is 1:1 to 1:5.

4. The electrolyte for a lithium secondary battery of claim 2, wherein the lithium imide salt comprises at least one of Li($CF_3SO_2$)$_2$N, Li($FSO_2$)$_2$N, or Li($CF_3CF_2SO_2$)$_2$N.

5. The electrolyte for a lithium secondary battery of claim 1, wherein the oligomer is present in an amount of 0.1 part by weight to 1 part by weight based on 100 parts by weight of the electrolyte.

6. The electrolyte for a lithium secondary battery of claim 1, wherein the first additive is represented by Formula 2A:

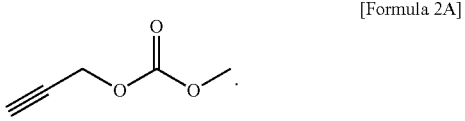

[Formula 2A]

7. The electrolyte for a lithium secondary battery of claim 1, wherein the first additive is present in an amount of 0.1 part by weight to 1 part by weight based on 100 parts by weight of the electrolyte.

8. The electrolyte for a lithium secondary battery of claim 1, wherein the organic solvent comprises dimethyl carbonate.

9. The electrolyte for a lithium secondary battery of claim 1, further comprising:
   a second additive,
   wherein the second additive comprises at least one of vinylene carbonate, ethylene sulfate, 1,3-propane sultone, fluorinated benzene, or $LiBF_4$.

10. The electrolyte for a lithium secondary battery of claim 9, wherein the second additive is present in an amount of 1 part by weight to 15 parts by weight based on 100 parts by weight of the electrolyte.

11. A lithium secondary battery comprising the electrolyte of claim 1.

* * * * *